United States Patent [19]

Man

[11] Patent Number: Plant 6,415

[45] Date of Patent: Nov. 22, 1988

[54] DISTINCT VARIETY OF BEGONIA PLANT NAMED PETRA

[75] Inventor: Jan Man, Lisse, Netherlands

[73] Assignee: Oglevee Associates, Inc., Connellsville, Pa.

[21] Appl. No.: 885,525

[22] Filed: Jul. 14, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new Begonia variety is characterized by its naturally short, compact plant with extensive and vigorously formed branches which are strong. The contrast between the orange flowers and dark green foliage is very pleasing. The new cultivar has a high tolerance to botrytis and powdery mildew.

1 Drawing Sheet

BACKGROUND OF THE NEW PLANT

The present invention comprises a new and distinct cultivar of *Begonia×hiemalis* known by the varietal name of Petra. The new cultivar is a natural sport of the cultivar Laressa. The new cultivar has the same foliage and plant form as Laressa, but the flower differs in that Laressa has a dark rose-pink tonality and Petra has an orange tonality.

The new cultivar was discovered in April of 1983 at Limaplant b.v. in Lisse, Holland; was first asexually reproduced by cuttings at Limaplant b.v. in Lisse, Holland; and has been repeatedly asexually reproduced by cuttings for Oglevee Associates, Inc. in Connellsville, Pa. It has been found to retain its distinctive characteristics through successive propagations.

The new cultivar is generally characterized by its naturally short, compact plant with extensive and vigorously formed branches which are strong. The contrast between the orange flowers and dark green foliage is very pleasing. The new cultivar has a high tolerance to botrytis and powdery mildew.

The new cultivar, when grown in a greenhouse in Connellsville, Pa., has a response time of 10 to 11 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Associates, Inc. in Connellsville, Pa. The plant history was taken on ten week plants blossomed under natural light in a greenhouse and grown under temperature conditions of 62° F. at night and 68° F. during the day. The plants were potted in a peat-lite mix and fertilized with a 100 ppm mixture of 15N-0P-15K. Color readings were taken indoors under 200 footcandles of cool white fluorescent tubes. Color references are to The R.H.S. Colour Chart of The Royal Horticultural Society of London, unless noted differently.

Botanical Classification: *Begonia×hiemalis.*

Flower:

- *Fully expanded.*—6 cm in diameter.
- *Borne.*—Compound dichasium (cyme).
- *Stems.*—Stem is strong and upright, main stem 12 mm in diameter; color yellow-green group 145A.
- *Form.*—Fully double. Each flower has 2 sepals, 7 petals, 7 petaloids (each group may vary ±1 structure).
- *Permanence.*—Long lasting bloom, bloom lasts an average of 2 weeks.

Color:

- *Tonality from a distance.*—Orange with red overtone.
- *Front of petals.*—Color gradient: light pink→orange; outer edge: red group 37A; inner area: orange-red group 33A.
- *Reverse of petals.*—Outer area: red group 41C.
- *Base of petals.*—Orange group 29A.
- *Throat.*—None.
- *Discoloration.*—None.
- *Other comments.*—Exact color reference difficult due to how old the flower is and how the plant was grown.

Petals:

- *Texture.*—Crepe paper like (gentle crinkles).
- *Appearance.*—Oval with color gradient: pink→orange.
- *Arrangement.*—Fully double.
- *Persistence.*—Very good flowering; high number of buds produced.
- *Fragrance.*—None.

Reproductive organs: All reproductive organs have modified into petaloids. Anthers, filament, pollen and style could not be observed.

Plant:

- *Form.*—Short and compact; internodes 1–2 cm apart; very good basal branching; strong stems give good self-support.
- *Growth.*—Very vigorous; growth may be modified by changing environmental conditions.
- *Height from soil line.*—14–16 cm in 10 weeks (no pinch, no cycocel).
- *Spread.*—30–32 cm in 10 weeks (no pinch, no cycocel).

Foliage:

*Size.*—Depends on age, position and environmental conditions. Average width of 8 cm and average length of 12 cm.

*Quantity.*—Very abundant.

*Shape.*—Acute tip with irregularly lobed attachment; edge is doubly serrated.

*Top side.*—Yellow-green group 147A.

*Underside.*—Yellow-green group 148B.

*Ribs and veins.*—Smooth on top, raised on bottom. Veins on lower side only area of leaf where tricomes (hairs) appear.

*Rib and vein color.*—Top side: yellow-green group 144D; bottom side: yellow-green group 145A.

*Margin.*—None.

*Stipules.*—None.

*Texture.*—Top: smooth, shiny, glabrous; bottom: matt finsh with raised veins.

I claim:

1. A new and distinct variety of Begonia characterized by its naturally short, compact plant with extensive and vigorously formed branches which are strong, the contrast between the orange flowers and dark green foliage being very pleasing, and high tolerance to botrytis and powdery mildew as herein shown and described and parts therefor.

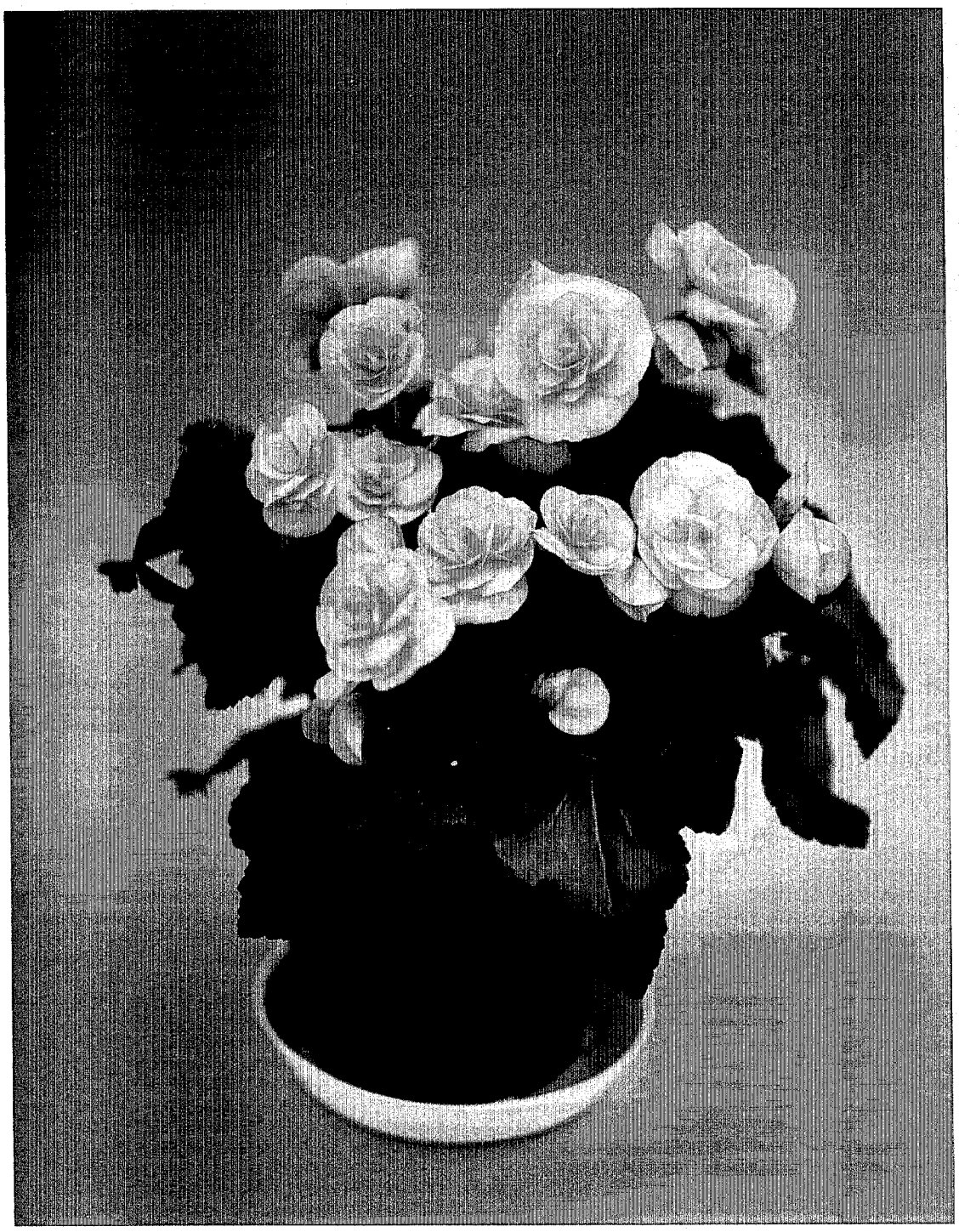

* * * * *